(12) United States Patent
Jenkins et al.

(10) Patent No.: US 11,453,859 B2
(45) Date of Patent: Sep. 27, 2022

(54) METHOD OF COATING SURFACES WITH NANOPARTICLES FOR BIOLOGICAL ANALYSIS OF CELLS

(71) Applicant: BioVentures, LLC, Little Rock, AR (US)

(72) Inventors: Samir V. Jenkins, Little Rock, AR (US); Robert J. Griffin, Little Rock, AR (US); Michael J. Borrelli, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 458 days.

(21) Appl. No.: 16/276,167

(22) Filed: Feb. 14, 2019

(65) Prior Publication Data

US 2019/0249136 A1 Aug. 15, 2019

Related U.S. Application Data

(60) Provisional application No. 62/630,575, filed on Feb. 14, 2018.

(51) Int. Cl.
| | |
|---|---|
| *C12N 5/00* | (2006.01) |
| *G01N 1/30* | (2006.01) |
| *C12Q 1/02* | (2006.01) |
| *G01N 33/50* | (2006.01) |

(52) U.S. Cl.
CPC .......... *C12N 5/0075* (2013.01); *C12Q 1/025* (2013.01); *G01N 1/30* (2013.01); *G01N 33/5005* (2013.01); *C12N 2531/00* (2013.01); *C12N 2533/00* (2013.01); *C12N 2533/20* (2013.01); *C12N 2539/00* (2013.01); *G01N 2001/305* (2013.01)

(58) Field of Classification Search
None
See application file for complete search history.

(56) References Cited

FOREIGN PATENT DOCUMENTS

WO    WO-2017039074 A1 *  3/2017  ............... C01G 7/00

OTHER PUBLICATIONS

Kalies, Stefan, et al. "Immobilization of gold nanoparticles on cell culture surfaces for safe and enhanced gold nanoparticle-mediated laser transfection." Journal of biomedical optics 19.7 (2014): 070505. (Year: 2014).*

Zhu, Yuejing, Mohankandhasamy Ramasamy, and Dong Kee Yi. "Antibacterial activity of ordered gold nanorod arrays." ACS applied materials & interfaces 6.17 (2014): 15078-15085. (Year: 2014).*

Shakila, V., and K. Pandian. "Preparation of gold nanoislands on various functionalized polymer-modified glass and ITO for electrochemical characterization of monolayer assembly of alkanethiols." Journal of Solid State Electrochemistry 11.2 (2007): 296-302. (Year: 2007).*

Hajduková, Natália, et al. "Chemically reduced and laser-ablated gold nanoparticles immobilized to silanized glass plates: preparation, characterization and SERS spectral testing." Colloids and Surfaces A: Physicochemical and Engineering Aspects 301.1-3 (2007): 264-270. (Year: 2007).*

Bhat, Rajendra R., and Jan Genzer. "Tuning the number density of nanoparticles by multivariant tailoring of attachment points on flat substrates." Nanotechnology 18.2 (2006): 025301. (Year: 2006).*

Zhang, Qiang, et al. "Fiber surface modification technology for fiber-optic localized surface plasmon resonance biosensors." Sensors 12.3 (2012): 2729-2741 (Year: 2012).*

* cited by examiner

*Primary Examiner* — Robert J Yamasaki
(74) *Attorney, Agent, or Firm* — Richard Blakely Glasgow

(57) ABSTRACT

A method of coating a surface with nanoparticles for biological analysis of cells that includes the steps of cleaning the surface with an oxidizing acid, treating the surface with an organosilane, coating the surface with nanoparticles, and then growing cells on the surface coated with the nanoparticles. The surface may be a glass surface, a silica-based surface, a plastic-based surface or a polymer-based surface. The nanoparticles may be gold-based nanomaterials.

6 Claims, 5 Drawing Sheets

30 um

METHOD OF COATING SURFACES WITH NANOPARTICLES FOR BIOLOGICAL ANALYSIS OF CELLS

CROSS-REFERENCE TO RELATED APPLICATIONS

This application claims the benefit of U.S. Provisional Application No. 62/630,575, entitled "Nanoparticle Coated Surface for Precision Nanobiology" and filed on Feb. 14, 2018. The complete disclosure of said patent application is hereby incorporated by reference.

STATEMENT REGARDING FEDERALLY SPONSORED RESEARCH OR DEVELOPMENT

This invention was made with government support from grant no. 01A-Award 1457888 awarded by the National Science Foundation. The government has certain rights in the invention.

BACKGROUND OF THE INVENTION

Local thermal therapy is an attractive, emerging treatment modality for various biomedical conditions requiring sterilization of pathological tissue features (clots, plaques, tumors, or infections). Gold or iron oxide nanoparticles are under intense investigation as thermal transducers due to their strong electromagnetic absorption, biocompatibility, and surface functionalizability. However, there is a major knowledge gap in the field due to a paucity of methods to determine the temperature and local biological effects around each stimulated nanoparticle. To date, characterizing the response to nanoparticle-induced heating generally relies on bulk solution temperature measurements and cell association values calculated after incubation with the particles. Multiple steps are involved in the preparation of these samples to ascertain cell association values; as a result, the quantification of the particle association with cells is indirect and experimentally determined. In addition to these preparatory steps, there is a wide distribution of particles per cell which further modulates the thermal dose received by individual cells, and is ultimately treated as a bulk average. As a result of these factors, correlating the thermal dose at the level of the particle vs. the bulk solution becomes a largely arbitrary and unreliable endeavor.

A current challenge for the validation of the mechanism of action of these materials upon non-invasive stimulation by light or magnetic field is the determination of "thermal dose." Thermal dose can be practically defined as the amount of heat received by a particular cell in a given time. Most in vitro studies rely on presumed values of cell uptake and only make use of the bulk solution temperature or even bulk solution heating to extrapolate biological consequences. In reality, the extreme variance on a per cell basis regarding particle uptake, combined with the relatively extreme heating at the nanoparticle surface limits the mechanistic utility of these studies. There is a further ambiguity regarding precise location of these particles within or outside of cells when added to growth medium in solution. Some researchers have calculated the surface temperature of nanomaterials to be greater than 1000° C. during laser irradiation, but both measuring and calculating these temperatures are nontrivial tasks. As a result, calculations of response to nanoregional heating are lacking, and the precise response to these extreme heating conditions is not well understood. A means to control the concentration and distribution of particles required to be in contact with the membrane of a cell for various biological effects to be obtained would be a major step forward toward accurately predicting and controlling thermal or other stimulated responses of nanomaterials Considering the cellular or matrix interactions, the close association of these particles with cells is critical to maximize biological effects. Traditional hyperthermic treatment uses multi-hour heating with a temperature change of only a few degrees above body temperature (<6° C.). Conversely, most nanoparticle heating studies utilize extremely short heating durations with analogous bulk temperature changes. However, the similar results indicate that while the time*temperature product—which estimates thermal dose—may be comparable, the duration and local heating effects cannot be.

Ionizing radiation is also a highly localized form of therapy relying of free radical stress to stimulate or kill cells. Meticulous dose planning is performed to minimize damage to normal tissue while maximizing the dose in the region of interest. Metal particles, because of their high Z value, act as X-ray absorbers, which results in increased generation of electrons at a local level. These electrons are then responsible for causing local cellular damage. At an in vitro single cell level, however, the underlying mechanisms of radiosensitization are still somewhat murky. The effective distance that the generated scatter electrons can travel is rarely considered, and it is only assumed that DNA damage must be involved. The effects of particle morphology or cellular uptake have only been cursorily investigated.

It would therefore be desirable to develop a method for uniformly coating surfaces with a variety of nanomaterials to enable quantitative biological analysis of radiosensitization, photothermal, and drug delivery effects induced by nanomaterials as well as cellular responses to topological changes. The surfaces may be glass or other silica-based surfaces, plastic-based surfaces, or polymer-based surfaces. This method was developed for laboratory settings to quantify nanomaterial effects, but it can be applied on an industrial scale as a surface upon which cell culture can be performed. Additionally, with minor modifications, this method can be used with a wide variety of metal and metal oxide nanomaterials. Specifically changing among thiol (strong metal binding), carboxylate (strong metal oxide binding), or amine (weaker metal and metal oxide binding) terminated organosilanes to promote attachment enables a variety of particle types to be used.

BRIEF SUMMARY OF THE INVENTION

Nanomaterials are of increasing interest in the field of biomedicine, but due to the complexities of biological systems and the diversity of materials, it is challenging to ascribe quantifiable effects to these materials. Towards that end, we have developed a methodology to controllably and uniformly coat surfaces with nanomaterials. Coverage density can be adjusted by variations in concentrations and experimental conditions. These surfaces can be sterilized and used for cell culture with a variety of cells. The topological differences in the surfaces affect cellular growth and differentiation. Additionally the materials are activatable, so quantitative measurements of the effects of laser exposure, radiation, magnetism, or drug conjugation can be performed.

Nanoparticles, particularly those made of high Z materials like gold or hafnium have shown some promise in radiosensitization approaches in murine models and clinical trials. The results, however, are largely phenomenological and lack mechanistic detail. There is evidence that a close association between cells and particles provides much greater radiosensitization. To better understand the true mechanism at play, gold nanocages were coated on glass coverslips to control the number of nanoparticles contacting each cell ab initio, enabling precise determination of a dose enhancement factor.

Methods: Gold nanocages of ~50 nm edge length were synthesized via galvanic replacement of a sacrificial silver nanocube template. These nanocages were then attached to glass coverslips that had been treated with (3 Mercaptopropyl)trimethoxysilane. Gold nanocages were used as a model system and can be substituted with a variety of nanomaterials of differing morphologies, including nanospheres, nanorods, nanourchines, nanocages, and any other morphology. Following deposition the surfaces were sterilized, and 4T1 murine breast tumor cells were seeded to the surface and allowed to adhere overnight. Due to the strong attachment to the surface, the nanomaterials are not taken up by the cells and provide topological differences on which the cells can adhere. This model system was then treated with 4 Gy of radiation (using a 150 keV source) and colony formation was assessed after 8 days. Cell size was measured using optical microscopy. Electron trajectories were simulated in water using the CASINO software with water as the substrate and electron energy of up to 50 keV.

Results: Surfaces were coated at densities of 0, 17, 34, or 68 $AuNC/um^2$. The cell contact area was found to be 308+/−15 $um^2$, indicating a total of 0, 0.52, 1.04, or 2.08×$10^4$ AuNC/cell+/−5%. The increasing concentration of AuNC was found to significantly enhance radiosensitization with a maximal dose enhancement factor or 2.25 occurring at ABC particle density. Interestingly, the inventors were able to correlate this value to a dose enhancement of $6.4 \times 10^{-5}$/AuNC, with a linear relationship between dose enhancement and number of AuNCs. Electrons generated from the particle upon interaction with the irradiation photons were predicted to be able to travel ~60 um with a 50 keV initial energy, indicating the electrons can pass completely through 4T1 cells with an average diameter of 30 uM while still maintaining enough energy to create biologically relevant collisions.

Conclusions: Gold nanocages were found to provide significant radiosensitization in an in vitro model. Initial results indicate that a particle density and sensitization are linearly related, and the electrons are likely affecting membrane, cytosol and nuclear compartments to induce cell death. Future surfaces will be treated with morphologically distinct gold structures, such as spheres, rods, and pyramids, or with clinically relevant materials of different compositions, such as carbon, iron oxide, hafnium oxide, and silica. The distance between the nucleus and surface will be increased with a polymer layer quantitatively assess the relative contribution of membrane vs. DNA damage in the observed effects of this approach, which will also be measured through manipulation of the cell cycle.

The present invention is directed to a method to generate uniform coatings of nanomaterials on surfaces and to adjust and control the coverage density of the nanomaterials by modifying the particle concentration, salinity, pH, or temperature during the coating step. This method is performed by thoroughly cleaning the surface with oxidizing acids and then treating the surface with functionalized organosilanes, which are then used as attachment points on the surface for the nanomaterials. Gold nanomaterials are described as a model system, but the method may alternatively include a variety of nanomaterials (including metallic and/or carbon- or polymer-based particles) and surface materials.

These and other features, objects and advantages of the present invention will become better understood from a consideration of the following detailed description of the preferred embodiments and appended claims in conjunction with the drawings as described following:

DETAILED DESCRIPTION OF THE INVENTION

Figure 1A:
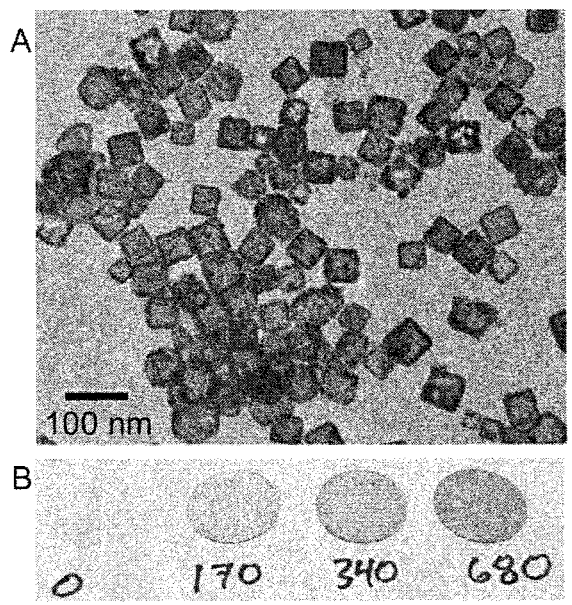
FIG. 1A is a TEM image of Au nanocages prior to coating on the surface.
Figure 1B:
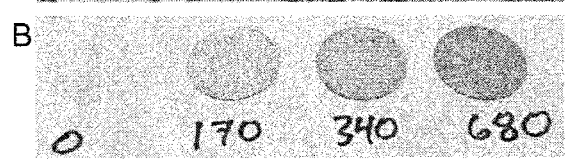
FIG. 1B is a photograph of the coverslips showing the changes in coverage density.
Figure 1C:
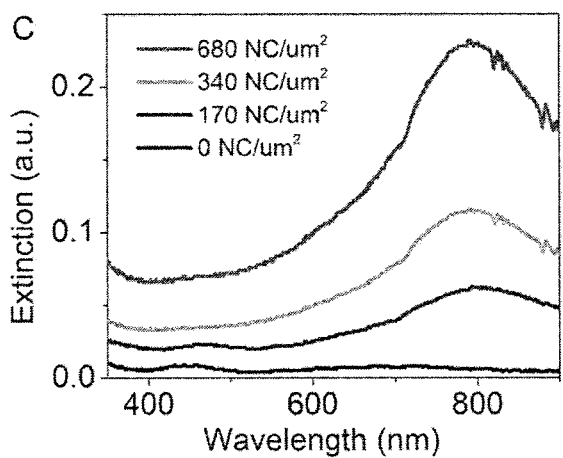
FIG. 1C is absorbance spectra of the various coverslips (top—680 $AuNC/um^2$; second to the top—340 $AuNC/um^2$; second to the bottom—170 $AuNC/um^2$; bottom—0 AuNC/$um^2$).
Figures 2A, 2B:
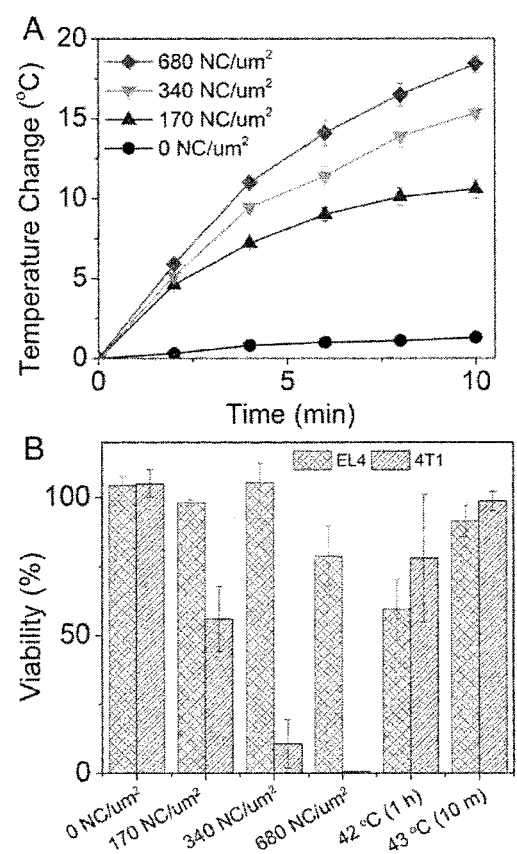
FIG. 2A is a heating profile of surfaces as a function of coverage density.
FIG. 2B is a bar chart showing cell viability of 4T1 cells grown on surfaces of different density normalized to the untreated control group.
Figure 3:
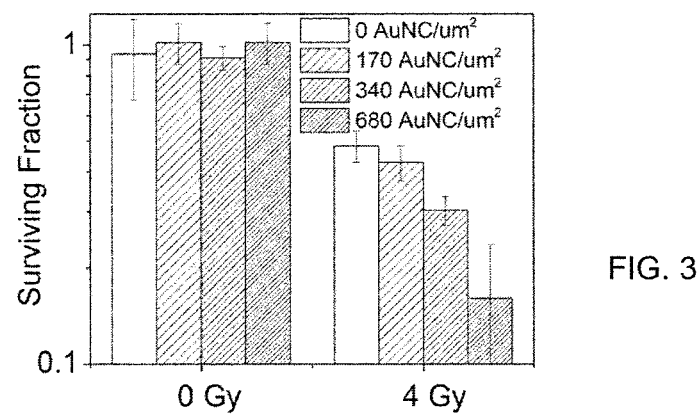
FIG. 3 is a bar chart showing clonogenic survival of 4T1 cells following 4 Gy radiation on different surface coverages. All values are normalized to 0 Gy on a standard tissue culture plate.
Figure 4:
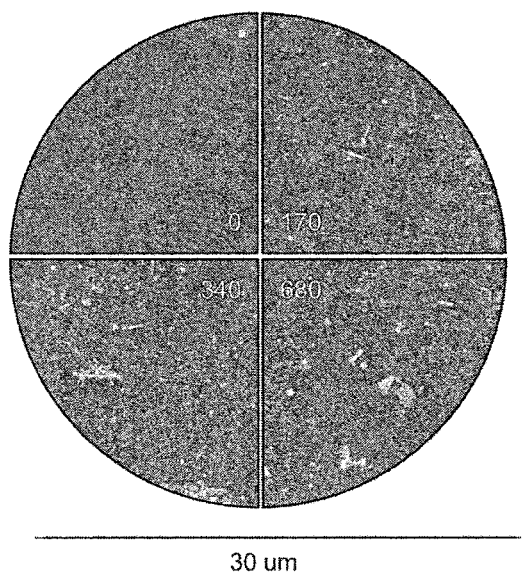
FIG. 4 is a scanning electron micrograph of gold particle coated surfaces at four coverage densities (in particle/$\mu m^2$). The diameter of the circle provides an approximate cross-sectional area of a cell.

With reference to FIGS. 1A-5C, the preferred embodiments of the present invention may be described. Gold nanocages were synthesized through a well-described method that would be well-known a person of ordinary skill in the art. FIG. 1A shows a transmission electron micrograph of gold nanocages after synthesis, and FIG. 1C shows extinction spectra following surface coating with different particle densities. They were used as a model nanomaterial for modification of glass surfaces. Glass coverslips were treated with piranha solution (3:1 conc. $H_2SO_4:H_2O_2$) at 60° C. for 1 hour, then washed thrice in methanol to remove residual acid. The coverslips were then immersed in a bath containing 10% 3-mercaptopropyltrimethoxysilane or 3-aminopropyltrimethoxysilane and allowed to react for 3 days at room temperature in a closed container. Following this reaction the coverslips were washed 3 times with methanol and 3 times with DI $H_2O$. The nanoparticles had already been dispersed in carbonate/bicarbonate buffer at a pH of 9 with 10 mM NaCl and were immediately added over the freshly prepared coverslips. They were then allowed to adhere for 2 days, followed by 3 washing cycles with $H_2O$ and air drying, yielding controllable surface coverage density. FIG. 4 show a scanning electron micrograph of gold nanocages coated surfaces at different coating densities. The circle is a rough approximation of the size of a cell, to provide a sense of scale. As necessary, adjustments to the pH (+/−1 unit) and salt concentration (+/−10 mM) are made to accommodate different nanoparticle formulations and prevent aggregation. These coverslips were sterilized using UV-C radiation in a standard BSL-2 hood. Cells were grown in normal media on the coverslips, and irradiation with X-radiation or near infrared radiation to more accurately determine dose responses. FIG. 3 shows clonogenic survival of breast cancer cells following 0 or 4 Gy of X-radiation on surfaces of differing coverage densities. All surviving fractions are normalized to 0 Gy on a standard tissue culture plate. FIG. 2A shows bulk heating effects as a function of particle coverage density during continuous wave NIR irradiation, and FIG. 2B shows cell viability of adherent [4T1] and suspension [EL4] cells grown on the surfaces of differing coverage densities and subjected to 10 min NIR irradiation. Bulk heating in a water bath [42° C. for 1 h or 43° C. for 10 min] is also included to illustrate differences. Surfaces are reusable and cells can be rapidly detached with dimethylsulfoxide without damage to the surface itself.

The inventors synthesized Au nanocages in high yield with high uniformity as shown in FIG. 1A. The optical properties of these particles can be readily tuned to maximize overlap with a variety of laser sources. The surfaces can be readily functionalized through the Au-thiol interaction with a variety of polymers and small molecules. Glass cover slips were treated with (3-mercaptopropyl)trimethoxysilane. The silane group integrates with the glass surface and the thiol groups serve as a stable attachment point for the Au nanocages via dative bonding between gold and sulfur. The coating appears highly uniform by optical microscopy, and the coverage density can be controlled during the synthetic process, as shown in FIG. 1B, by adjusting the particle concentration, pH, salinity, and temperature of the reaction, which yielded coverage densities of $6.8 \times 10^2$, $3.4 \times 10^2$, and $1.7 \times 10^2$ AuNC/um$^2$. The absorbance increases as a function of the coverage density as shown in FIG. 1C, which will be correlated to the coverage density as determined by electron microscopy.

The surfaces were treated with laser heating using an 808 nm continuous wave laser for 10 min. The laser power output was measured before and after the experiments. The heating as a function of coverage density for 1.5 W (1 W/cm$^2$) laser power is shown in FIG. 2A. Cell viability of adherent (4T1) and suspension (EL4) murine cells as a function of heating is shown in FIG. 2B. The massive loss of cell viability after the 10 min heating cycle stands in stark contrast to viability measurements made following 60 min of heating in a water bath set to the highest measured temperature (42° C.) only for the adherent cells, while the suspension cells responded similarly to bulk heating.

The 4T1 cells were also grown on the surfaces and allowed to adhere for 4 h prior to radiation treatment of 4 Gy using a 150 kV irradiator. Because radiation can take several cell doublings prior to the biological effects becoming apparent, the effectiveness was measured using clonogenic survival. The results of this initial study are shown in FIG. 3, and clearly show particle density dependence and thus number of nanoparticles (specifically nanocages are shown) in contact per cell (in this case tumor cell) dependent radiosensitization.

Figures 5A, 5B:
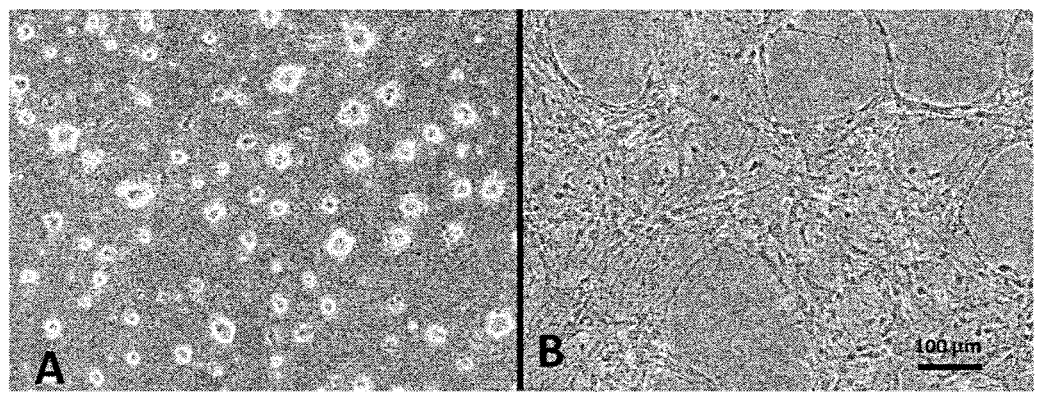
FIGS. 5A-5C are micrographs showing neural stem cells that were subcultured onto laminin-coated surfaces with (A) 0% or (B) 1% FBS in the medium or, (C) on matrigel with no FBS.
Figure 5C:
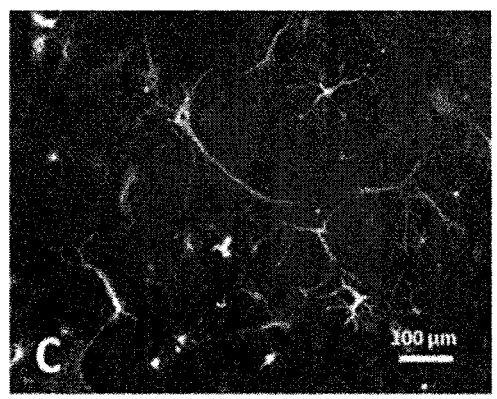

As described above, this innovative method to securely attach gold nanoparticles to glass by first functionalizing the glass with thiol groups and then depositing the particles under basic pH and sterilizing the surfaces prior to cell deposition. Scanning electron microscopy shows a highly uniform distribution, particularly with regard to the size of a cell as shown in FIG. 4. For this study, the inventors used hollow gold cubes that were roughly 50 nm across. These cubes are deposited in a single layer across the surface, and the absorbance value is directly proportional to the coverage density of the cubes as shown in FIG. 1C. The wavelength of maximum absorbance can be readily matched with laser light, which enables precise control of heating at the surface by modulating the fluence and optical dose. Indeed the particles function like very small heaters and are significantly hotter than the bulk temperature effect. The inventors demonstrated this change in heating through photothermal killing of adherent cells, while under identical conditions suspension cells were minimally affected as shown in FIG. 2B. The cell killing of adherent cells did not match with bulk heating effects, indicating a strong effect from the nanoparticles themselves. Neural stem cells can also be grown on these surfaces, and the coverage density has significant effects on the ability of these cells to adhere and grow, indicating an important response to the topology of the surface itself. These surfaces show great potential for directing neural differentiation with mild stresses and environmental cues. To date, the inventors have demonstrated growth of large numbers of differentiating neurons using matrigel or laminin coated coverslips and varying the fetal serum content as shown in FIGS. 5A-5C. These cells can later be transferred to the innovative surfaces for implantation studies. While these initial studies show promise, the coverslips are tedious and expensive to fabricate and cannot be reused.

Further Investigation—Example 1

Fabrication and Characterization of the Surfaces:

Au nanocages will be synthesized using the galvanic replacement reaction and thoroughly characterized by TEM, UV-Vis spectroscopy, and mass analysis. Particle-coated surfaces will be generated through covalent conjugation following silanization of glass coverslips. The particle coverage density will be determined using atomic force microscopy, scanning electron microscopy, photoacoustic microscopy, and direct optical measurements. The stability of these surfaces in culture media will be interrogated with and without laser treatment. Variations in the synthesis parameters will be used to control the density of particles on the surface.

Thermal Properties and Cellular Response:

The thermal response of these surfaces to laser irradiation will be thoroughly modeled. Bulk temperatures for wells containing the surface and cell culture medium will be directly measured via thermocouple and infrared probes at a variety of particle coverage densities and laser power densities. Additionally, due to nanoregional heating effects, the theoretical temperature at the coverslip surface will be modeled using molecular dynamics simulations and corresponding state analysis. From these data, the thermal gradient in various media emanating from this surface will be further modeled. A variety of cells will be grown on these surfaces and the cell sizes will be measured using microscopy to determine the number of particles per cell.

Radiosensitization:

To establish a baseline, several different coating densities of the same nanoparticle will be investigated clonogenically. The long-term cell killing effects will be evaluated for different coating densities, and a sample of cells will be acquired for a number of radiation doses for protein and RNA analysis, which will be used to validate the immediate biological effect. The distance dependence of these effects will be modeled theoretically, and these calculations will be validated experimentally by coating varying thicknesses of laminin above the surface of the nanoparticles to create a physical barrier. The same surface generating chemistry will be used to adhere a variety of nanoparticles to the surface using similar coverage densities to measure the effects of morphology on radiosensitization. AuNCs possess nearly right-angle corners and relatively flat surfaces. As such, nanospheres of different sizes (curvatures) will be tested for their radiosensitizing capacity, as will similarly-sized nanorods. The size of the rods can be controlled synthetically and by extension the curvature of the body and cap of the rods. Compton scattering is largely dependent on the quantity of high Z atoms and the number of dangling bonds, the latter of which is directly related to curvature. As such, investigating the role of morphology in a highly controlled matter can generate extremely valuable data on the radiosensitizing capacity of metal nanoparticles. These data will be used to determine the amount of dose enhanced cell death that a variety of different types of Au nanomaterials can generate.

This project seeks to develop solution phase methods to generate highly uniform nanoparticle coated surfaces for cell culture. It then seeks to precisely quantify the nanoparticle doses needed to achieve particular biological outcomes. Initial studies will be limited to several particle types, but the methodology is anticipated to translate to a large variety of materials. The primary and immediate effort of this project, however, is to determine the precise number of particles necessary to elicit a biological effect, which should be able to inform in vivo work with nanomaterials.

Further Investigation—Example 2

Damage to neural activity can occur in many ways, and often this damage is lasting due to an inability to generate new neurons. Damage occurs from a variety of events that typically result in the loss of oxygen to particular regions of the brain. A means to differentiate neural stem cells into functional neurons in high yield is needed, and the ability to perform such differentiation in vitro would allow for the increased production of neurons that could later be implanted. Nanotechnology offers one potential route to generate these neurons. Nanoparticles are typically one-thousandth or less of the size of a cell, and gold nanoparticles are particularly appealing because they can be rapidly synthesized in a wide variety of morphologies at yields that enable large scale experiments. Additionally, gold has demonstrated excellent stability and biocompatibility, and the surface can be modified readily through the strong bonding between thiol groups and gold atoms. The particles also can be externally activated through the use of light to generate heat and acoustic waves. The inventors have developed a method to synthesize highly uniform nanoparticle-coated glass surfaces that can support cellular growth. Modifications to these surfaces will be interrogated to determine the optimal system to develop and reliable source of functional neurons.

The ultimate goal of this project is to develop reusable artificial extracellular matrix surfaces to generate neurons in high yield and implant them into damaged tissue to restore function. Differentiation into neurons can be accomplished through a variety of means, though they are often costly and labor intensive. Neural stem cells exist within niches throughout the brain, but the selective differentiation of these endogenous cells in a therapeutic setting remains challenging. This can be worked around through in vitro differentiation and implantation of functional neurons. A variety of cytokines and chemokines can induce this differentiation, including IL6, IL10, and interferon γ. The extracellular matrix has also been shown to play a significant role in selective differentiation. Factors including the protein composition, elasticity, and topology of the matrix can direct differentiation down a target path. Additionally, physical stimuli have been shown to promote differentiation, including mild heating, vibration, electrical stimulation, hypoxia, and even the pattern of laminin coating on a substrate can further direct differentiation. Heating and vibration are particularly relevant as these stimuli can be exogenously induced by harnessing the plasmonic properties of gold nanomaterials, which generate heat and acoustic waves upon irradiation with visible light. Additionally, exosomes (small, secreted, extracellular vesicles that are used for intercellular communication) have been implicated in guiding differentiation. Exosomes can be isolated from cultured cells in vitro, and can be found in nearly all biological fluids, particularly blood and cerebrospinal fluid as well as saliva. Exosomes contain unique cargoes of protein, RNA, and DNA, which are used to signal other cells to respond in particular fashions. Interestingly, the exosomes found in snake venom may be a source of highly concentrated neural growth factor and other components as was observed several decades ago during a period when the Nobel Prize was awarded for the discovery of NGF. Whether or not the exosomes from venom could improve and sustain neuronal differentiation in our setting will be investigated. In general, exosomes derived from tumors can promote growth, and exosomes within the blood can serve an immune signaling function to recruit and activate particular cells. More critically, exosomes derived from differentiated cells can be used to induce selective differentiation in progenitor stem cells. Often some of these neural cells will differentiate into astrocytes under similar conditions. The astrocytes are proliferative, which results in them overtaking cell culture in vitro and reducing the availability of viable neurons. As such maximizing the yield of functional neurons with novel approaches such as our stimuli-responsive surfaces and select exosome samples is essential to developing a viable in vitro system to generate functional neurons.

Methods: Synthesis of Nanoparticle Coated Surfaces with Varying Coverage Density and Nanoparticle Morphology, and Optical Stimulation to Induce Differentiation to Neurons:

Glass coverslips will be activated with piranha solution, washed, and then functionalized with 3-mercaptotrismethoxysilane. A variety of nanoparticle morphologies including spheres, rods, and cubes will be suspended in a buffer with pH between 8 and 10 and incubated over these surfaces. Varying the concentration of particles used will result in different particle coverage densities. Combined with the different nanomaterial morphologies this will allow the creation of a library of different topologies on which neural stem cells will be grown. These surfaces will be characterized optically, as well as by scanning electron microscopy, photothermal microscopy, and mass analysis to quantify to coverage density, uniformity and topology of the surfaces.

Rat neural stem cells (rNSCs) will be acquired from ATCC along with the appropriate growth medium. Initially they will be grown on the various topologies and after two weeks will be assessed using confocal microscopy and flow cytometry to determine differentiation ratios for neurons and glial cells. Specifically, cells staining positive for βIII tubulin or MAP-2 will be considered neurons and cells staining positive for GFAP will be considered glial cells. This will be used to determine promising candidate topologies. RNSCs will be grown on these candidates and treated with low laser fluences to attempt to stimulate improved differentiation. Cells on these surfaces will also be analyzed by flow cytometry and confocal microscopy. Cells grown on promising surfaces will also be interrogated using patch-clamp microelectrode recording to determine their action potential and functionality in our collaborator's laboratory.

Covalent Conjugation of Bioactive Molecules and Polymers to the Gold Surface to Further Improve Neural Differentiation:

Candidate surfaces developed will have the gold surfaces modified in a variety of ways and the neuronal differentiation and functionality will be quantified similarly as described above. Covalent functionalization will be accomplished using direct thiol anchoring of biomolecules to the gold surface or conjugation with mercaptopropionic acid followed by N-hydroxysuccinimide coupling to yield a peptide bond. Biomolecules that will be used include cytokines such as IL-6, IL-10, and interferon γ. Exosomes will be isolated from several cell types and biological sources including neurons, tumor cells, plasma, cerebrospinal fluid, and snake venom (known to possess high levels of NGF). These exosomes will be either homogenized and the lysate covalently attached or the whole exosomes will be attached using NHS coupling. Any promising exosome samples will have the protein cargo characterized, and the outputs will be analyzed to determine the relative expression of various proteins to determine the unique candidate biomolecules for coatings. Additionally, more traditional coatings such as fibronectin, polylysine, and gelatin will be coated on particle coated surfaces and pristine coverslips to determine if the topography and improve the effectiveness of known drivers of differentiation. Several polymers will also be investigated including poly(ethyleneimine) to provide positive charge, poly(ethylene glycol) to provide a neutral charge, and poly (acrylic acid) to provide a negative charge.

Implantation of Grown Neurons into a Rat Brain to Undo Ischemic Stroke Damage:

Ischemic stroke will be induced in rats using the medial cerebral artery (MCA) method. Briefly, a suture is threaded through the common carotid artery to occlude the vessels resulting in development of reproducible ischemic lesions and penumbra. These lesions will be confirmed using magnetic resonance imaging. This model was selected due to its mimicry of human ischemic stroke and its reproducibility. After confirmation of the lesion, the neural activity and behavior of the rats will be assessed as described. The most functional neurons developed in this study will be implanted surgical into the damaged tissue and the neural function and behavior of the animals will be monitored and quantified to determine the integration of the new cells and the tolerability of the system. Following euthanasia, the brains of the animals will be harvested, fixed, and assessed for pathology. An adequate sample number for statistical validity will be estimated and studied by consulting with our biostatistics core at our institution.

The present invention has been described with reference to certain preferred and alternative embodiments that are intended to be exemplary only and not limiting to the full scope of the present invention as set forth in the appended claims.

REFERENCES

1. Eliasson, M. J. L.; Huang, Z.; Ferrante, R. J.; Sasamata, M.; Molliver, M. E.; Snyder, S. H.; Moskowitz, M. A., Neuronal Nitric Oxide Synthase Activation and Peroxynitrite Formation in Ischemic Stroke Linked to Neural Damage. *The Journal of Neuroscience* 1999, 19 (14), 5910.
2. Dreaden, E. C.; Alkilany, A. M.; Huang, X.; Murphy, C. J.; EI-Sayed, M. A., The golden age: gold nanoparticles for biomedicine. *Chemical Society Reviews* 2012, 41 (7), 2740-2779.
3. Eck, W.; Craig, G.; Sigdel, A.; Ritter, G.; Old, L. J.; Tang, L.; Brennan, M. F.; Allen, P. J.; Mason, M. D., PEGylated Gold Nanoparticles Conjugated to Monoclonal F19 Antibodies as Targeted Labeling Agents for Human Pancreatic Carcinoma Tissue. *ACS Nano* 2008, 2 (11), 2263-2272.
4. Jenkins, S. V.; Nedosekin, D. A.; Miller, E. K.; Zharov, V. P.; Dings, R. P. M.; Chen, J.; Griffin, R. J., Galectin-1-based tumour-targeting for gold nanostructure-mediated photothermal therapy. *International Journal of Hyperthermia* 2018, 34 (1), 19-29.
5. Reubinoff, B. E.; Pera, M. F.; Fong, C.-Y.; Trounson, A.; Bongso, A., Embryonic stem cell lines from human blastocysts: somatic differentiation in vitro. *Nature Biotechnology* 2000, 18, 399.
6. Discher, D. E.; Mooney, D. J.; Zandstra, P. W., Growth Factors, Matrices, and Forces Combine and Control Stem Cells. *Science* 2009, 324 (5935), 1673.
7. Leipzig, N. D.; Xu, C.; Zahir, T.; Shoichet, M. S., Functional immobilization of interferon-gamma induces neuronal differentiation of neural stem cells. *Journal of Biomedical Materials Research Part A* 2010, 93A (2), 625-633.
8. Guilak, F.; Cohen, D. M.; Estes, B. T.; Gimble, J. M.; Liedtke, W.; Chen, C. S., Control of Stem Cell Fate by Physical Interactions with the Extracellular Matrix. *Cell Stem Cell* 2009, 5 (1), 17-26.
9. Ling, Z. D.; Potter, E. D.; Lipton, J. W.; Carvey, P. M., Differentiation of Mesencephalic Progenitor Cells into Dopaminergic Neurons by Cytokines. *Experimental Neurology* 1998, 149 (2), 411-423.
10. Saha, K.; Keung, A. J.; Irwin, E. F.; Li, Y.; Little, L.; Schaffer, D. V.; Healy, K. E., Substrate Modulus Directs Neural Stem Cell Behavior. *Biophysical Journal* 2008, 95 (9), 4426-4438.
11. Huang, C. C.; Narayanan, R.; Alapati, S.; Ravindran, S., Exosomes as biomimetic tools for stem cell differentiation: Applications in dental pulp tissue regeneration. *Biomaterials* 2016, 111, 103-115.
12. Angeletti, R. H., Studies on the nerve growth factor (NGF) from snake venom molecular heterogeneity. *Journal of Chromatography A* 1968, 37, 62-69.
13. Scarpettini, A. F.; Bragas, A. V., Coverage and Aggregation of Gold Nanoparticles on Silanized Glasses. *Langmuir* 2010, 26 (20), 15948-15953.
14. Xue, Y.; Li, X.; Li, H.; Zhang, W., Quantifying thiol-gold interactions towards the efficient strength control. *Nature Communications* 2014, 5, 4348.
15. Solanki, A.; Shah, S.; Memoli, K. A.; Park, S. Y.; Hong, S.; Lee, K.-B., Controlling differentiation of neural stem cells using extracellular matrix protein patterns. *Small (Weinheim an der Bergstrasse, Germany)* 2010, 6 (22), 2509-2513.
16. Silva, G. A.; Czeisler, C.; Niece, K. L.; Beniash, E.; Harrington, D. A.; Kessler, J. A.; Stupp, S. I., Selective Differentiation of Neural Progenitor Cells by High-Epitope Density Nanofibers. *Science* 2004, 303 (5662), 1352.
17. Johansson, C. B.; Momma, S.; Clarke, D. L.; Risling, M.; Lendahl, U.; Frisén, J., Identification of a Neural Stem Cell in the Adult Mammalian Central Nervous System. *Cell* 1999, 96 (1), 25-34.
18. Hayar, A.; Gu, C.; Al-Chaer, E. D., An improved method for patch clamp recording and calcium imaging of neurons in the intact dorsal root ganglion in rats. *J Neurosci Methods* 2008, 173 (1), 74-82.
19. Kore, R. A.; Edmondson, J. L.; Jenkins, S. V.; Jamshidi-Parsian, A.; Dings, R. P. M.; Reyna, N. S.; Griffin, R. J., Hypoxia-derived exosomes induce putative altered pathways in biosynthesis and ion regulatory channels in glioblastoma cells. *Biochemistry and Biophysics Reports* 2018, 14, 104-113.
20. Brown, A. T.; Arthur, M. C.; Nix, J. S.; Montgomery, J. A.; Skinner, R. D.; Roberson, P. K.; Borrelli, M.; Culp, W. C., Dodecafluoropentane Emulsion (DDFPe) Decreases Stroke Size and Improves Neurological Scores in a Permanent Occlusion Rat Stroke Model. *The open neurology journal* 2014, 8, 27-33.
21. Culp, W. C.; Woods, S. D.; Skinner, R. D.; Brown, A. T.; Lowery, J. D.; Johnson, J. L. H.; Unger, E. C.; Hennings, L. J.; Borrelli, M. J.; Roberson, P. K., Dodecafluoropentane emulsion decreases infarct volume in a rabbit ischemic stroke model. *Journal of vascular and interventional radiology: JVIR* 2012, 23 (1), 116-121.
22. Shetty, A. K.; Hattiangady, B., Grafted Subventricular Zone Neural Stem Cells Display Robust Engraftment and Similar Differentiation Properties and Form New Neurogenic Niches in the Young and Aged Hippocampus. *Stem Cells Transl Med* 2016, 5 (9), 1204-15.
23. Yokota, K.; Kobayakawa, K.; Kubota, K.; Miyawaki, A.; Okano, H.; Ohkawa, Y.; Iwamoto, Y.; Okada, S., Engrafted Neural Stem/Progenitor Cells Promote Functional Recovery through Synapse Reorganization with Spared Host Neurons after Spinal Cord Injury. *Stem Cell Reports* 2015, 5 (2), 264-277.

We claim:

1. A method of coating a surface with a gold nanoparticle for biological analysis of a cell, comprising the steps of:
   a. cleaning said surface with an oxidizing acid;
   b. treating said cleaned surface with 3-mercaptopropyltrimethoxysilane;
   C. coating said treated surface with said nanoparticle comprising a step of adding a dispersion to said surface, wherein said dispersion comprises said nanoparticle and has a pH between 8 and 10; and
   d. growing said cell on said surface coated with said nanoparticle.

2. The method of claim 1, wherein said surface is a glass surface, a silica-based surface, a plastic-based surface or a polymer-based surface.

3. The method of claim 1, wherein said nanoparticle comprises a nanocage.

4. The method of claim 1, further comprising the step of conducting a biological analysis of said cell.

5. The method of claim 4, wherein said biological analysis comprises exposing said cell to radiation.

6. The method of claim 1, wherein said pH is 9.

* * * * *